United States Patent
Pang et al.

(10) Patent No.: US 6,352,508 B1
(45) Date of Patent: Mar. 5, 2002

(54) TRANSDUCER MOTION COMPENSATION IN MEDICAL DIAGNOSTIC ULTRASOUND EXTENDED FIELD OF VIEW IMAGING

(75) Inventors: Linyong Pang, Stanford; John A. Hossack, Palo Alto, both of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/384,707

(22) Filed: Aug. 26, 1999

Related U.S. Application Data

(63) Continuation-in-part of application No. 09/196,986, filed on Nov. 20, 1998.

(51) Int. Cl.$^7$ .............................................. A61B 8/00
(52) U.S. Cl. ................................................. 600/443
(58) Field of Search ................................. 600/437, 443, 600/447, 459, 466–467

(56) References Cited

U.S. PATENT DOCUMENTS

| | | | | |
|---|---|---|---|---|
| 5,538,004 A | * | 7/1996 | Bamber | 128/916 |
| 6,117,081 A | * | 9/2000 | Jago et al. | 600/443 |
| 6,152,878 A | * | 11/2000 | Nachtomy et al. | 600/467 |
| 6,162,174 A | * | 12/2000 | Friemel | 600/447 |

* cited by examiner

*Primary Examiner*—Francis J. Jaworski
(74) *Attorney, Agent, or Firm*—Brinks Hofer Gilson & Lione

(57) ABSTRACT

An extended field of view medical diagnostic ultrasound image is corrected for distortion associated with azimuthal motion of the transducer. The actual azimuthal motion is determined from the original, motion-distorted estimate of transducer motion, and this actual transducer motion is then used to correct dimensional errors in the extended field of view image.

14 Claims, 3 Drawing Sheets

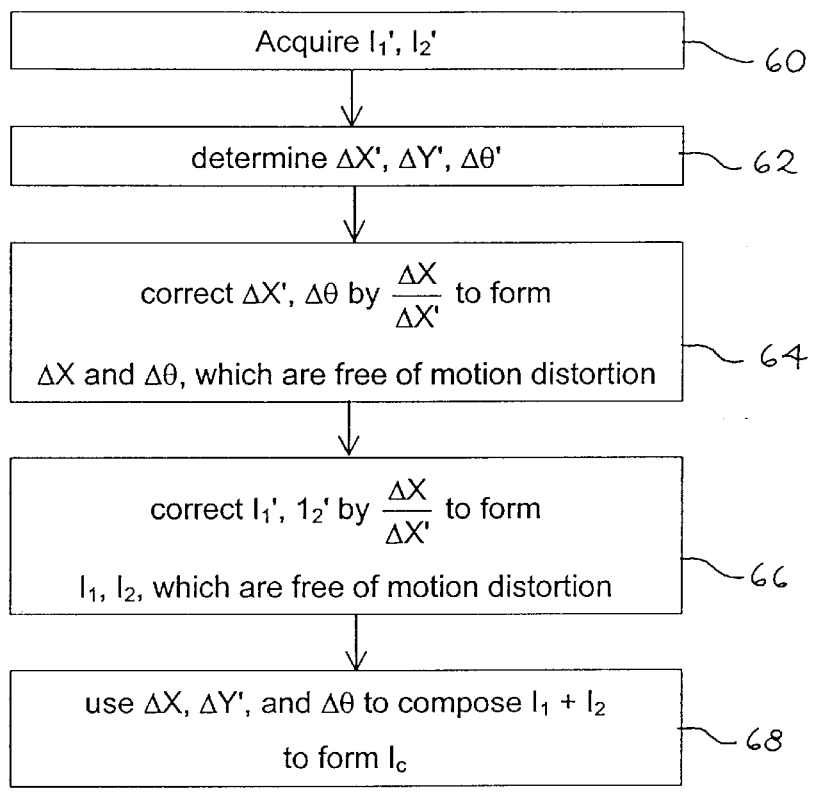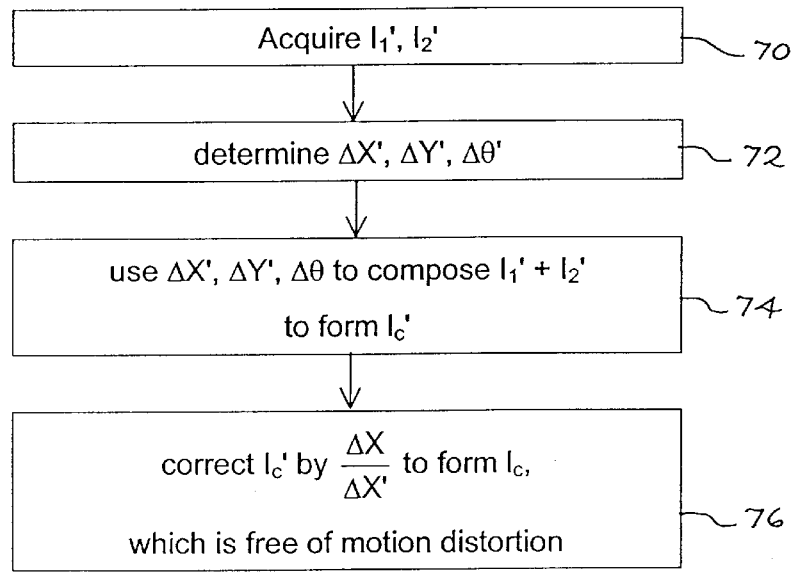

TRANSDUCER MOTION COMPENSATION IN MEDICAL DIAGNOSTIC ULTRASOUND EXTENDED FIELD OF VIEW IMAGING

CROSS REFERENCE TO RELATED APPLICATION

This application is a continuation-in-part of copending U.S. patent application Ser. No. 09/196,986, filed Nov. 20, 1998, which is hereby incorporated by reference in its entirety.

BACKGROUND

This invention is related to medical ultrasonic diagnostic imaging, and more specifically to methods that compose multiple substantially coplanar image frames into an extended field of view image.

Extended field of view imaging is disclosed for example in U.S. Pat. No. 5,557,286 (Weng), as well as in U.S. patent application Ser. Nos. 09/196,986 and 09/196,987, both assigned to the assignee of the present invention. These patent documents disclose several different methods for aligning successively acquired substantially coplanar images to form the desired extended field of view.

U.S. Pat. No. 5,910,114 (Nock) discloses a method for correcting the geometry of ultrasonic images acquired with a moving transducer. The disclosed method uses scanning parameter information beyond the information contained in the acquired images themselves.

U.S. patent application Ser. No. 09/196,986, naming the same inventors as the present application, recognizes that transducer motion can be a source of distortion in the acquired images.

A need presently exists for improved methods for assessing and correcting transducer motion distortion in acquired images used for extended field of view imaging.

SUMMARY

By way of introduction, the preferred embodiments described below provide methods for accurately determining the distortion caused by transducer motion during the acquisition of multiple substantially coplanar images for an extended field of view. The methods described below significantly reduce dimensional errors in the extended field of view image, thereby enhancing the dimensional accuracy of the multi-frame, composed image.

The present invention is defined by the following claims. This paragraph has been provided merely by way of introduction, and is not intended to define the scope of the following claims.

BRIEF DESCRIPTION OF THE DRAWINGS

FIG. 8 is a flow chart of a first preferred embodiment of this invention.

FIG. 9 is a flow chart of a second preferred embodiment of this invention.

DETAILED DESCRIPTION OF THE PRESENTLY PREFERRED EMBODIMENTS

A. General Discussion

1. The Source of Transducer Motion Distortion

Figure 1:
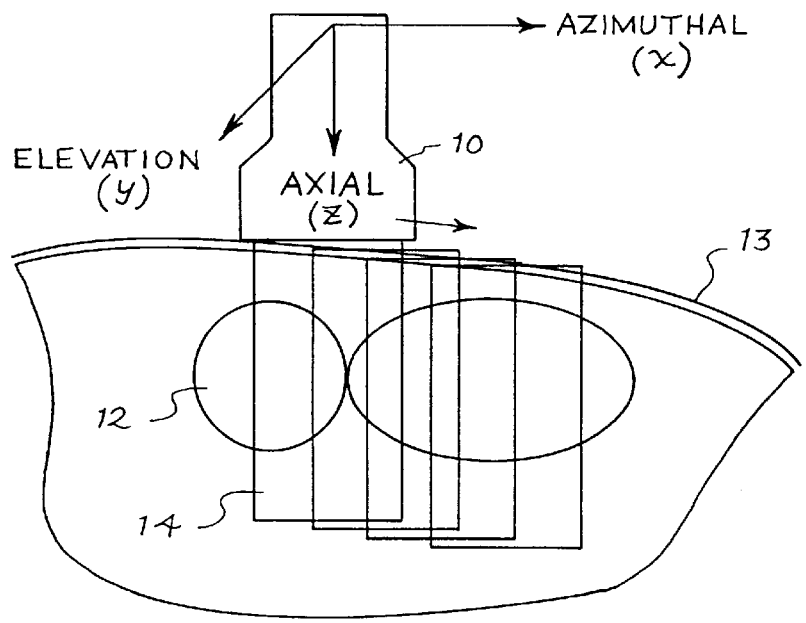
FIG. 1 is a schematic diagram showing the manner in which multiple, substantially coplanar images are acquired.

FIG. 1 illustrates a general scanning setup suitable for extended field of view imaging. In FIG. 1, a medical diagnostic ultrasound transducer array 10 is shown moving along the skin 13 of the body of a subject. In this example, the motion is along the azimuthal direction of the transducer array 10. As the transducer array 10 is moved, a succession of substantially coplanar images 14 are acquired frame-by-frame. Internal structures, such as organs of the subject, are shown schematically at 12.

In conventional extended field of view imaging, the transducer motion between successive images is estimated and relative motion vectors for consecutive images are computed. Multiple ones of the acquired images, or portions of these images, are then composed into a single extended field of view image using the relative motion vectors. As described below in conjunction with FIG. 2, such relative positions are inaccurate because the images themselves are stretched or compressed due to the effects of transducer motion in the azimuthal direction.

Figure 2:
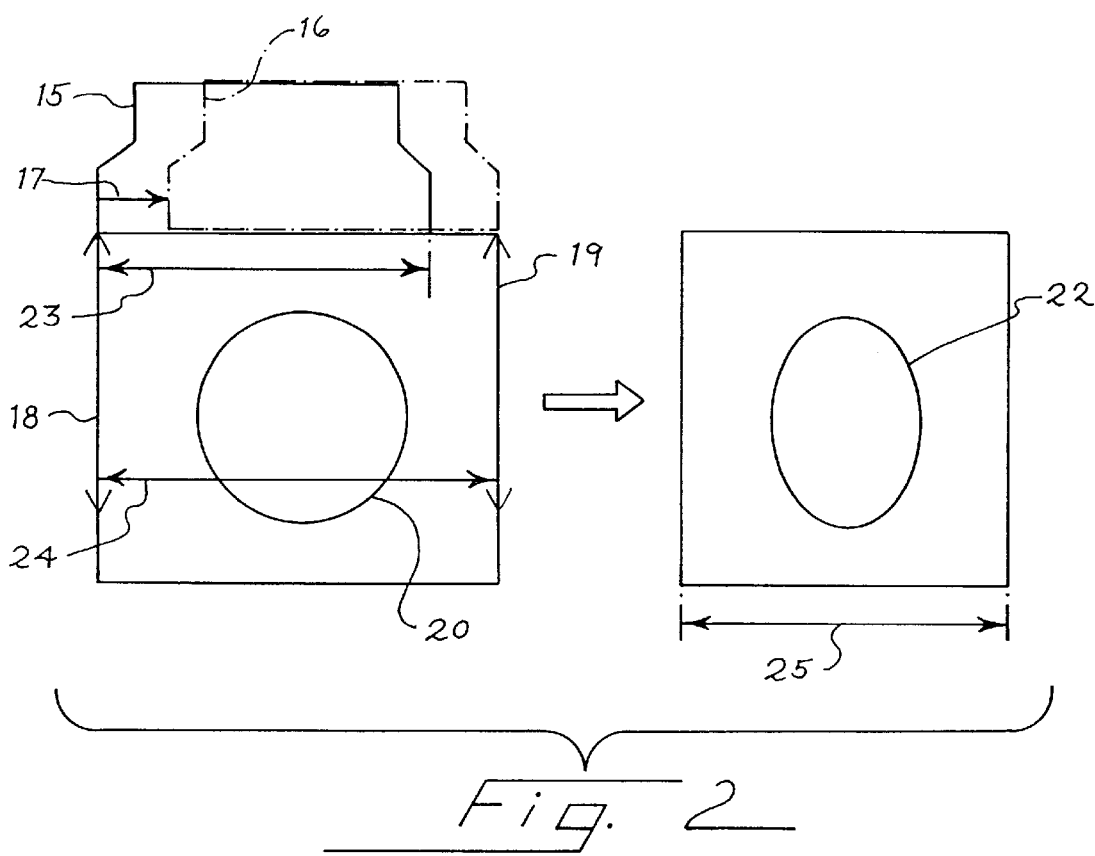
FIG. 2 is a schematic diagram illustrating the source of transducer motion distortion in the acquired images of FIG. 1.

FIG. 2 illustrates such transducer motion distortion. In FIG. 2, the reference symbol 15 is used to designate the transducer array at the start of acquisition of a specific image frame, and the reference symbol 16 is used to indicate the position of the transducer array at the end of the acquisition of this frame. The motion of the transducer array between the start and end of the frame is indicated by the vector 17, and this motion corresponds to the actual azimuthal displacement $\Delta X$ discussed below.

The image frame shown in FIG. 2 is acquired with multiple scan lines 20 including a first scan line 18 and a last scan line 19. Thus, in this embodiment the image frame is acquired using scan lines that progressively move from left to right in the view of FIG. 2. Reference symbol 20 indicates the actual, undistorted shape of a target. The assumed width the image W is indicated at 23, and this dimension corresponds to the actual width of the image for the case of no azimuthal transducer motion. However, in the case of transducer motion from left to right as shown in FIG. 2, the actual region that is scanned between the initial scan line 18 and the final scan line 19 extends over the width $W+\Delta X$, as shown at 24.

As shown on the left hand side of FIG. 2, at the time the final scan line 19 is acquired, the transducer array has moved some amount distance, $\Delta X$ in this example. Since the imaging system typically does not take into account the motion of the transducer array, the width of the acquired images will not account for transducer motion. For this reason, the image size of objects of the acquired image will be the same as the actual size of the object if the transducer array is held motionless on the subject, but they will not be equal if the transducer array is moved. As shown on the right hand side of FIG. 2, if transducer motion is not corrected, the acquired image shows a distorted image 22 of the target. This is because the acquired image has a width W as shown at 25, instead of the width $W+\Delta X$, as shown at 24.

As discussed below, transducer motion along the azimuthal direction also distorts the estimate of transducer rotation.

2. The Recovery of the Actual Transducer Motion from the Acquired Images

For simplicity, the following discussion will first consider the case of a linear transducer array. In this discussion, the symbol W is used for the width of an acquired image obtained when the transducer array is maintained in a stationary location with respect to the target. Now the transducer array is moved along its azimuthal direction as described above and a series of substantially coplanar images is acquired. First and second images are matched by any suitable method to determine $\Delta X'$, the apparent displacement or motion in the azimuthal direction between the two acquired images.

The present inventors have recognized that $\Delta X'$ is inaccurate because the widths of the images acquired by the transducer array are inaccurate due to the transducer motion distortion described above. In the following discussion, the term $\Delta X$ will be used for the true or actual, undistorted motion between the two selected images along the azimuthal direction.

A sign function is defined as follows:

$$\text{sign} = \begin{cases} +1, & \text{if transducer array scans from left to right} \\ -1, & \text{if transducer array scans from right to left} \end{cases} \quad (2.1)$$

The distorted width of the image is equal to W and the true or actual width of the image is equal to $W + \text{sign} \cdot \Delta X$, as described above in conjunction with FIG. 2. Thus, a motion distortion factor (the ratio of the true pixel width to the motion-distorted pixel width) is given by the following equation:

$$\text{Motion Distortion factor} = \frac{W + \text{sign} \cdot \Delta X}{W}. \quad (2.2)$$

Note that $\Delta X$ is an unknown in this equation, but that $\Delta X'$ can readily be determined by matching or correlating the two selected images.

Since the motions $\Delta X$ and $\Delta X'$ are estimated in units of pixels, $$\text{Motion Distortion factor} = \frac{\Delta X}{\Delta X'} = \frac{W + \text{sign} \cdot \Delta X}{W}. \quad (2.3)$$

The actual azimuthal motion $\Delta X$ can be obtained by solving equation 2.3:

$$\Delta X = \frac{\Delta X'}{1 - \frac{\Delta X'}{W} \cdot \text{sign}} \quad (2.4)$$

In equation 2.4, W is known, $\Delta X'$ is estimated, and $\Delta X$ can therefore easily be computed. Note that the above solution is independent of the frame rate and the aperture size, and that it requires only information contained in the ultrasonic images themselves. No knowledge is required of scanning parameters such as scanning speed, frame rate, or aperture size of the transducer.

In extended field of view imaging there are three components of transducer motion to be considered: transducer displacement in the azimuthal direction, transducer displacement in the axial direction, and in-plane transducer rotation. The foregoing discussion has related to the motion correction for transducer translation in the azimuthal direction. Translation of the transducer array in the axial direction is usually quite small compared to translation in the azimuthal direction, because the transducer array is typically moved along the patient's body. For this reason, the motion distortion associated with transducer motion in the axial direction is ignored in this discussion. However, in-plane transducer rotation is also affected by azimuthal transducer motion.

Figures 3, 4, 5:
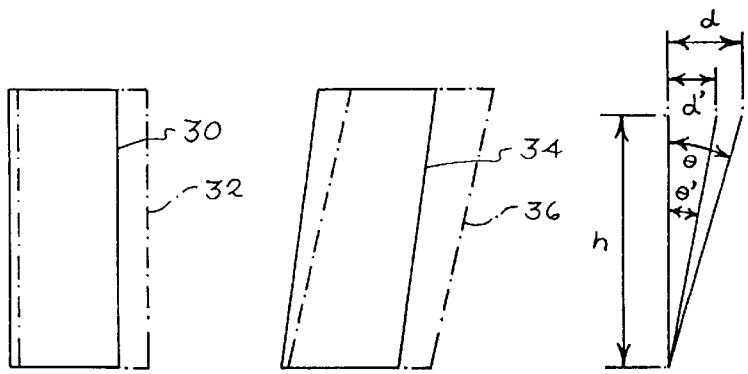
FIGS. 3, 4 and 5 are schematic diagrams illustrating translational and rotational transducer motion distortion.

FIG. 3 shows a rectangular image 30 that is motion-distorted due to azimuthal transducer translation, and the dotted lines show the true imaged region 32. FIGS. 4 and 5 illustrate rotation distortion due to rotation of the transducer array in the azimuthal plane.

In FIG. 4, the imaged region 34 and the actual region 36 are shown when there is significant transducer in-plane rotation. As shown in FIG. 5, the actual in-plane transducer rotation $\theta$ is somewhat larger than the motion-distorted estimate of transducer in-plane rotation $\theta'$ in this example.

Since the angles of in-plane transducer rotation are typically quite small, they can be approximated by:

$$\theta = \frac{d}{h}. \quad (2.5)$$

The azimuthal offset d at the top of the image is distorted by azimuthal motion of the transducer. The ratio of the true offset d to the estimated offset d' is equal to the ratio of pixel size distortion:

$$\frac{d}{d'} = \frac{\Delta X}{\Delta X'}. \quad (2.6)$$

As discussed above, image distortion in the axial direction can be ignored for this analysis, and therefore, $$\frac{\theta}{\theta'} = \frac{d}{d'}, \quad (2.7)$$

where $\theta'$ and $\theta$ are the angle of transducer in-plane rotation before and after the transducer motion error compensation, respectively. Finally, the rotation angle $\theta'$ can be corrected by the following approximate formula:

$$\theta = \theta' \frac{\Delta X}{\Delta X'}. \quad (2.8)$$

The motion corrections derived above use a linear transducer array for illustration. In such a linear transducer array, the motion errors for all axial positions are the same. For other types of transducer arrays, the motion errors at different axial positions may be different because the physical width of the B-mode image varies as a function of the axial position.

Figures 6, 7:
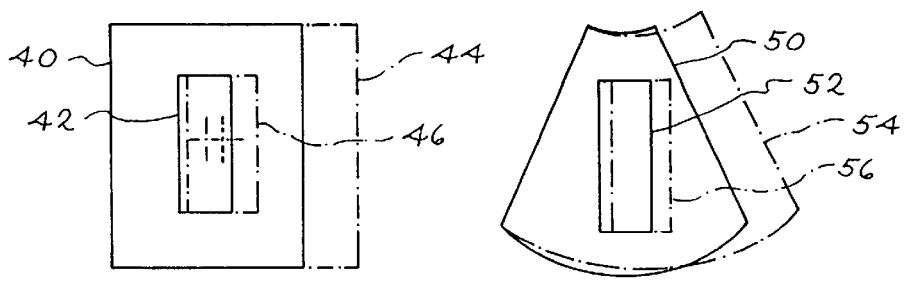
FIGS. 6 and 7 are schematic diagrams illustrating transducer motion correction for linear and curvilinear transducers, respectively.

As shown in FIG. 6, the image region 40 has a rectangular shape with a linear transducer array, and the azimuthal translational motion corrections at any axial position are the same when the transducer has only a translation motion. In FIG. 6, the solid lines 40, 42 represent the acquired image and a rectangular box in the acquired image, respectively, when the transducer array is in motion in the azimuthal direction, and the dashed lines 44, 46 illustrate the true shapes of the acquired image 40 and the rectangular box 42, respectively.

FIG. 7 shows the case for a curvilinear transducer array, where the rectangular box is no longer a rectangle in shape in the distorted image. In FIG. 7, reference symbols 50, 52 indicate an acquired image and a rectangular box of the acquired image, respectively, and the dotted line elements 54, 56 represent the actual or true shapes of the elements 50, 52, respectively. The variation of motion distortion as a function of axial position for a curvilinear transducer array is a second order effect, and the motion correction formulas derived above can be used with good results for curvilinear transducer arrays.

When the angle between the left bound and the right bound of the image is no longer a small angle, equation 2.8 is preferably modified as follows. To obtain the true rotation, let us first consider the apparent translation at the top and bottom of the image, namely $\Delta x'_1$, and $\Delta x'_2$. Using a small angle approximation, we have $$\Delta x'_1 = \Delta x' - \frac{h}{2} \theta', \quad (2.9)$$

$$\Delta x'_2 = \Delta x' + \frac{h}{2} \theta', \quad (2.10)$$

where h is the height of image, and $\theta'$ is the apparent rotation estimated at the center of the image.

Now applying the translation compensation formula (equation 2.4), we can calculate the true translation at the top and bottom of the image, respectively.

$$\Delta x_1 = \frac{\Delta x'_1}{1 - \frac{\Delta x'_1}{W_1} \cdot \text{sign}}, \quad (2.11)$$

$$\Delta x_2 = \frac{\Delta x'_2}{1 - \frac{\Delta x'_2}{W_2} \cdot \text{sign}}, \quad (2.12)$$

where $W_1$ and $W_2$ are the width of the image at the top and the bottom when the transducer is held motionless.

Once $\Delta x_1$ and $\Delta x_2$ are known, the true rotation along the center of the image, $\theta$, can be calculated from $\Delta x_1$ and $\Delta x_2$ by the following small angle rotation approximation formula:

$$\theta = \frac{\Delta x_2 - \Delta x_1}{h}. \quad (2.13)$$

Once the motion-distorted estimates of motion $\Delta X'$, $\Delta\theta'$ have been corrected as described above to generate the true or actual motion estimates $\Delta X$, $\Delta\theta$, the size of the images or portions of the images used to compose the extended field of view image are preferably also corrected. Ignoring second order errors, the image or a portion of an image is scaled by a factor equal to $\Delta X/\Delta X'$ in the azimuthal direction. This can be conveniently done by scaling azimuthal pixel width by $\Delta X/\Delta X'$.

The discussion to date has dealt with the normally occurring case in which the ultrasonic imaging system scans sequentially from transducer element 1 to transducer element N and then repeats with negligible interframe delay. The correction methods of this invention can also be used with ultrasonic imaging systems that employ an interframe block delay. Such delays may occur for example if the frame rate is limited to a lower value than the maximum possible value, or if individual frames are triggered, as for example in response to an EKG signal. As another example, color Doppler acquisition often imposes a delay interval between adjacent frames.

In the case where the frame-to-frame time interval is substantially longer than the time required to acquire an individual frame, then the ratio of equation 2.2 is preferably adjusted appropriately, approximately by multiplying the term sign $\cdot \Delta X$ in equation 2.2 by a factor equal to the ratio of the time to acquire a single frame divided by the frame-to-frame time interval. A more precise derivation of this adjustment to equation 2.2 is provided in attached Appendix A.

Figure 10:
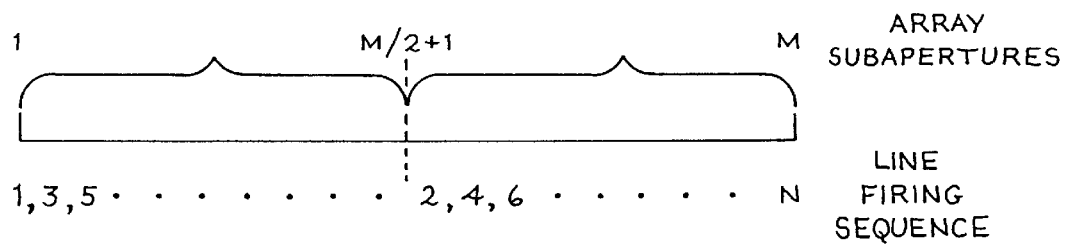
FIGS. 10 and 11 are schematic diagrams of two irregular scan line firing sequences.
Figure 11:
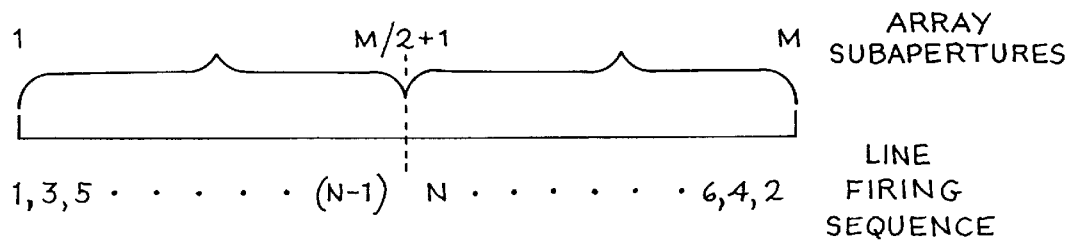

The present invention can also readily be adapted for use with ultrasonic imaging systems that use non-sequential scan line patterns. FIGS. 10 and 11 show two additional scan line firing sequences. In the sequences of FIGS. 10 and 11, the full aperture of M transducer elements is divided into left and right sub-apertures. Lines are alternately fired in each of these two sub-apertures to create the entire frame of scan lines. In the firing sequence of FIG. 10, each sub-aperture is scanned from left to right. In the scan sequence of FIG. 11, the sub-aperture are scanned from the outside to the inside of the frame. In FIGS. 10 and 11 the indicated numbers refer to the scan line firing sequence.

These irregular scanning sequences may be preferred because successive scan lines are not positioned adjacent to one another and multipulse interference is therefore reduced.

In the case of the scan line firing sequences of FIGS. 10 and 11, one solution is to perform motion analysis using only the left-hand side of the frame (i.e., scan lines 1, 3, 5 . . . (N−1)). Note that the line firing sequence of FIG. 11 is such that if the left-hand side of the frame is compressed during acquisition, then the right-hand side of the frame is extended when the transducer is moving in the right direction. For this reason, motion-related distortion corrections of opposite polarities are applied to the left-hand side and the right-hand side of the frame of FIG. 11. In these examples, the duration of line firing for scan lines 1 through N is approximately equal to the frame-to-frame interval, and therefore the motion distortion equation of equation 2.2 can be used. Note that for the left or right half-image, W is equal to one half the image width.

B. Specific Embodiments

FIGS. 8 and 9 are flow charts of two specific embodiments of the method of this invention. Table 1 summarizes the notation used in FIGS. 8 and 9.

TABLE 1

| | |
|---|---|
| $I_1'$, $I_2'$ | 1st and 2nd distorted frames as acquired, respectively |
| $I_1$, $I_2$ | 1st and 2nd frames corrected for transducer motion distortion, respectively |
| $I_c'$, $I_c$ | distorted and corrected composite frames, respectively |
| $\Delta X'$, $\Delta X$ | distorted and corrected azimuthal displacement between 1st and 2nd frames, respectively |
| $\Delta\theta'$, $\Delta\theta$ | distorted and corrected in-plane rotation between 1st and 2nd frames, respectively |
| $\Delta Y'$, $\Delta Y$ | distorted and corrected axial displacement between 1st and 2nd frames, respectively |

The first act in this method is to acquire two motion-distorted images $I_1'$ and $I_2'$ (60). These images can be acquired using any suitable ultrasonic imaging system (digital or analog) and any suitable transducer array (linear or curvilinear, 1, 1.5 or 2-dimensional) using any suitable transducer technology.

Next, the motion-distorted images $I_1'$ and $I_2'$ are correlated with one another at 62 to determine motion-distorted estimates of azimuthal motion ($\Delta X'$), axial motion ($\Delta Y'$), and in-plane rotation ($\Delta\theta'$). Any suitable correlation algorithm can be used as long as a good match is obtained between corresponding features in the distorted images $I_1'$, $I_2'$. For example, any of the correlation methods described in the patent documents discussed above can be used.

At 64, the motion-distorted estimates $\Delta X'$ $\Delta\theta'$ are corrected by a factor $\Delta X/\Delta X'$ to form $\Delta X$ and $\Delta\theta$, which are azimuthal and rotational motion estimates that are free of azimuthal transducer motion distortion. For example, Equation 2.4 described above can be used to determine ΔX, using any suitable computer.

At 66, the motion-distorted images $I_1'$, $I_2'$ are corrected or scaled in the azimuthal direction by a scaling factor $\Delta X/\Delta X'$ to form corrected images $I_1$, $I_2$, which are free of distortion due to azimuthal motion of the transducer.

At 68, the corrected motion estimates ΔX and Δθ are used, in combination with an estimate of axial motion ΔY', to compose $I_1$ and $I_2$, thereby forming a composite image $I_c$ which provides an extended field of view. As discussed above, in this embodiment ΔY is not corrected for transducer motion distortion, in view of the relatively low axial velocities of the transducer.

FIG. 9 relates to a second preferred embodiment in which motion-distorted, substantially coplanar images $I_1'$, $I_2'$ are acquired at 70. The acquired images are correlated with one another to determine the apparent azimuthal displacement ΔX' and the apparent in-plane rotation Δθ' therebetween. These initial portions of the method of FIG. 9 can be identical to the corresponding portions of the method of FIG. 8 described above, and all of the alternatives described there can be used here as well.

At 74, the motion-distorted estimates ΔX', Δθ' are used, in combination with an estimate of axial motion ΔY', to compose the distorted images $I_1'$ and $I_2'$, thereby forming a composite, extended field of view image $I_c'$. After composition, the composite extended field of view image $I_c'$ is corrected in the azimuthal direction by a scale factor $\Delta X/\Delta X'$ to form $I_c$, which is free from transducer azimuthal motion distortion.

FIGS. 8 and 9 relate to the correction and composition of two image frames. In actual practice the methods of these figures are used to correct and compose a large number of image frames to produce the desired extended field of view. The method of FIG. 8 can be used to determine a separate correction for each frame in a series of frames, except for the last frame which may use the same correction as the next-to-last frame.

The embodiments of FIGS. 8 and 9 provide the advantage that the extended field of view image is corrected for transducer azimuthal motion distortion. The embodiment of FIG. 8 provides the further advantage of correcting the measured azimuthal motion ΔX' and the measured rotation Δθ' for motion distortion associated with azimuthal movement of the transducer. In this way, dimensional errors in the extended field of view image are significantly reduced, thereby providing an important advantage.

C. Alternatives

It will be recognized that a wide variety of changes and modifications can be made to the preferred embodiments described above, and that many alternative technologies can be used to implement these embodiments. For example, the correcting and composing acts of FIGS. 8 and 9 can be implemented with any suitably programmed computer, using any desired computer language. A wide variety of programming techniques and specific algorithms can be used. The correction of the extended field of view image can be performed either before or after the individual frames are composed. In some embodiments, the dimensional distortion of the extended field of view image associated with transducer azimuthal motion can be corrected without correcting the motion vector ΔX'. Alternately, the motion vector ΔX' can be corrected as described above, without correcting the azimuthal dimensional scale of the extended field of view image. In some embodiments, the motion vector can be corrected as described above, even when the motion vector is not used for formation of an extended field of view image.

Similarly, the uncorrected motion vector ΔX' can be used to correct the dimension of the acquired image. Images may also be corrected by adjusting the displayed scale of an image or the caliper scale used with an image. In addition, more accurate formulas can be derived to correct the image distortion for non-linear transducer arrays. If desired, the methods described in Hossack et al. U.S. Pat. No. 5,873,830 can be used in combination with the methods described above, as can the methods and transducer arrays described in U.S. patent application Ser. No. 08/916,585, both assigned to the assignee of the present invention.

In view of the many changes and modifications that can be made to the preferred embodiments described above, it is intended that these preferred embodiments be understood as only a few examples of the many forms that this invention can take. For this reason, it is only the following claims, including all equivalents, that are intended to define the scope of this invention.

What is claimed is:

1. A method for forming a composite medical diagnostic ultrasound image from a plurality of substantially coplanar medical diagnostic ultrasound images, said method comprising the following acts:

(a) determining an apparent displacement between first and second ones of the coplanar images;

(b) determining a transducer motion distortion factor based essentially on image information included in the coplanar images;

(c) correcting the apparent displacement with the transducer motion distortion factor;

(d) correcting at least a portion of the coplanar images with the transducer motion distortion factor; and (e) using the corrected apparent displacement to register the corrected portion of the coplanar images.

2. The method of claim 1 further comprising the following acts:

(f) determining an apparent rotation between said first and second ones of the coplanar images; and (g) correcting the apparent rotation with the transducer motion distortion factor.

3. The method of claim 2 wherein (e) comprises the additional act of:

(e1) using the corrected apparent rotation to register the corrected portion of the coplanar images.

4. The method of claim 2 wherein act (g) comprises:

(e1) using the following formula to determine θ, the corrected rotation between the first and second images:

$$\theta = \frac{\Delta x_2 - \Delta x_1}{h},$$

where h=image height, $$\Delta x_1 = \frac{\Delta x_1'}{1 - \frac{\Delta x_1'}{W_1} \cdot \text{sign}},$$

$$\Delta x_2 = \frac{\Delta x_2'}{1 - \frac{\Delta x_2'}{W_2} \cdot \text{sign}},$$

$W_1$=stationary image width at top of image,
$W_2$=stationary image width at bottom of image, $$\Delta x'_1 = \Delta x' - \frac{h}{2}\theta',$$

$$\Delta x'_2 = \Delta x' + \frac{h}{2}\theta',$$

$\Delta x'$=apparent translation at center of image,
$\theta'$=apparent rotation between first and second images.

5. The method of claim 1 wherein act (b) comprises the act of:
   (b1) setting the transducer motion distortion factor as a function of $$\frac{\Delta X'}{1 - \frac{\Delta X'}{W} \cdot \text{sign}},$$

where $\Delta X'$ is the apparent azimuthal displacement and $W$ is the width of the first image at a position where $\Delta X'$ is estimated.

6. A method for forming a composite medical diagnostic ultrasound image from a plurality of substantially coplanar medical diagnostic ultrasound images, said method comprising the following acts:
   (a) determining an apparent displacement between first and second ones of the coplanar images;
   (b) using the apparent displacement to register at least some of the coplanar images;
   (c) determining a transducer motion distortion factor based essentially on image information included in the coplanar images; and
   (d) correcting the registered coplanar images with the transducer motion distortion factor.

7. The method of claim 6 further comprising the following act:
   (e) determining an apparent rotation between said first and second ones of the coplanar images.

8. The method of claim 6 wherein act (b) further comprises the act of:
   (b1) using the apparent rotation to register at least some of the coplanar images.

9. The method of claim 6 wherein act (c) comprises the act of:
   (c1) setting the transducer motion distortion factor as a function of $$\frac{\Delta X}{\Delta X'},$$

where $$\Delta X = \frac{\Delta X'}{1 - \frac{\Delta X'}{W} \cdot \text{sign}},$$

and $W$ is equal to a width of the first coplanar image at a position where $\Delta X'$ is estimated.

10. A method for determining displacement between at least first and second substantially coplanar medical diagnostic ultrasound images, said method comprising the following acts:
    (a) determining an apparent displacement between the first and second images;
    (b) determining a transducer motion distortion factor based essentially on image information included in the coplanar images; and
    (c) correcting the apparent displacement with the transducer motion distortion factor.

11. The method of claim 10 further comprising the following acts:
    (d) determining an apparent rotation between the first and second images; and
    (e) correcting the apparent rotation with the transducer motion distortion factor.

12. The method of claim 11 wherein act (e) comprises
    (e1) using the following formula to determine $\theta$, the corrected rotation between the first and second images:

$$\theta = \frac{\Delta x_2 - \Delta x_1}{h},$$

is where $h$=image height, $$\Delta x_1 = \frac{\Delta x'_1}{1 - \frac{\Delta x'_1}{W_1} \cdot \text{sign}},$$

$$\Delta x_2 = \frac{\Delta x'_2}{1 - \frac{\Delta x'_2}{W_2} \cdot \text{sign}},$$

$W_1$=stationary image width at top of image,
$W_2$=stationary image width at bottom of image, $$\Delta x'_1 = \Delta x' - \frac{h}{2}\theta',$$

$$\Delta x'_2 = \Delta x' + \frac{h}{2}\theta',$$

$\Delta x'$=apparent translation at center of image,
$\theta'$=apparent rotation between first and second images.

13. A method for determining displacement between at least first and second substantially coplanar medical diagnostic ultrasound images, said method comprising the following acts:
    (a) determining an apparent displacement between the first and second images;
    (b) determining a transducer motion distortion factor based essentially on image information included in the coplanar images and timing information regarding image acquisition time and delay time between adjacent ones of the coplanar images; and
    (c) correcting the apparent displacement with the transducer motion distortion factor.

14. A method for determining displacement between at least first and second substantially coplanar medical diagnostic ultrasound images, said method comprising the following acts:
    (a) determining an apparent displacement between the first and second images;
    (b) determining a transducer motion distortion factor based essentially on image information included in the coplanar images and a non-regular timing sequence of the coplanar images; and
    (c) correcting the apparent displacement with the transducer motion distortion factor.

* * * * *